(12) United States Patent
Sharnez et al.

(10) Patent No.: US 11,958,882 B2
(45) Date of Patent: Apr. 16, 2024

(54) METHODS DIRECTED TO CRYSTALLINE BIOMOLECULES

(71) Applicant: AMGEN INC., Thousand Oaks, CA (US)

(72) Inventors: Rizwan Sharnez, Mead, CO (US); William Trieu, Agoura Hills, CA (US); Marc A. Caporini, Cambridge, MA (US); Ron C. Kelly, Thousand Oaks, CA (US); Neill Burt, Denver, CO (US); Laura Nicholson, Boulder, CO (US); Twinkle R. Christian, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1248 days.

(21) Appl. No.: 16/494,165

(22) PCT Filed: Mar. 14, 2018

(86) PCT No.: PCT/US2018/022387
§ 371 (c)(1),
(2) Date: Sep. 13, 2019

(87) PCT Pub. No.: WO2018/170098
PCT Pub. Date: Sep. 20, 2018

(65) Prior Publication Data
US 2020/0157141 A1    May 21, 2020

Related U.S. Application Data

(60) Provisional application No. 62/476,359, filed on Mar. 24, 2017, provisional application No. 62/471,358, filed on Mar. 14, 2017.

(51) Int. Cl.
*C30B 7/10* (2006.01)
*A61K 39/395* (2006.01)
(Continued)

(52) U.S. Cl.
CPC ........ *C07K 1/306* (2013.01); *A61K 39/39591* (2013.01); *B01J 8/20* (2013.01);
(Continued)

(58) Field of Classification Search
CPC ..... A61K 39/39591; C07K 1/306; B01J 8/20; B01J 8/38; C30B 7/00; C30B 7/10;
(Continued)

(56) References Cited

U.S. PATENT DOCUMENTS 6,264,989 B1    7/2001    Kato et al.
9,279,133 B2    3/2016    Mehta et al.
(Continued)

FOREIGN PATENT DOCUMENTS

WO    2005/005460 A1    1/2005
WO    2010008563 A1    1/2010
(Continued)

OTHER PUBLICATIONS

European Application 21203497.9 Extended Search Report (dated Feb. 3, 2022) 13 pages.
(Continued)

*Primary Examiner* — Robert M Kunemund
(74) *Attorney, Agent, or Firm* — Melissa E. Karabinis

(57) ABSTRACT

Disclosed herein are methods of preparing a composition comprising crystalline biomolecules, for example, crystalline antibodies. In exemplary embodiments, the method comprises forming a fluidized bed of crystalline biomolecules using, for example, a counter-flow centrifuge to exchange buffer and/or to concentrate the crystalline biomolecules in a solution. Also provided are methods of detecting crystalline biomolecules and/or amorphous biomolecules in a sample.

10 Claims, 7 Drawing Sheets

(51) Int. Cl.

| | | |
|---|---|---|
| *B01J 8/20* | (2006.01) | |
| *B01J 8/38* | (2006.01) | |
| *C07K 1/30* | (2006.01) | |
| *C30B 7/00* | (2006.01) | |
| *C30B 30/04* | (2006.01) | |
| *G01N 24/08* | (2006.01) | |
| *C30B 30/00* | (2006.01) | |
| *C30B 30/02* | (2006.01) | |
| *G01N 24/00* | (2006.01) | |
| *G01R 33/20* | (2006.01) | |
| *G01R 33/46* | (2006.01) | |

(52) U.S. Cl.
CPC .................................... *B01J 8/38* (2013.01); *C30B 7/00* (2013.01); *C30B 7/10* (2013.01); *C30B 30/04* (2013.01); *G01N 24/087* (2013.01); *C30B 30/00* (2013.01); *C30B 30/02* (2013.01); *G01N 24/00* (2013.01); *G01N 24/008* (2013.01); *G01R 33/20* (2013.01); *G01R 33/46* (2013.01)

(58) Field of Classification Search
CPC ......... C30B 30/00; C30B 30/04; C30B 30/02; C30B 29/58; G01N 24/00; G01N 24/087; G01N 24/008; G01R 33/20; G01R 33/46
See application file for complete search history.

(56) References Cited

U.S. PATENT DOCUMENTS

| | | | |
|---|---|---|---|
| 2005/0045094 A1 | 3/2005 | Ng et al. | |
| 2007/0208163 A1* | 9/2007 | Jensen .................. | A61K 38/28 530/399 |
| 2011/0207222 A1 | 8/2011 | Mehta et al. | |

FOREIGN PATENT DOCUMENTS

| | | |
|---|---|---|
| WO | 2013/096778 A1 | 6/2013 |
| WO | 2016/010927 A1 | 1/2016 |

OTHER PUBLICATIONS

Luyts, et al, "Relative importance of moisture migration and amylopectin retrogradation for pound cake crumb firming" Food Chemistry, vol. 141, Issue 4, pp. 3960-3966, Dec. 15, 2013.

Martin, et al., "Preparation of protein nanocrystals and their characterization by solid state NMR", Journal of Magnetic Resonance 165, pp. 162-174, 2003.

Matulova, et al., "Degradation of Wheat Straw by Fibrobacter succingenes S85: a Liquid-and Solid-State Nuclear Magnetic Resonance Study", Applied and Environmental Microbiology, vol. 71, No. 3, pp. 1247-1253, Mar. 2004.

Japanese Patent Application No. 2019-550646 Office Action dated Jul. 5, 2022.

Barb, A. W. and Prestegard, J. H., "NMR analysis demonstrates immunoglobulin G N-glycans are accessible and dynamic," *Nat Chem Biol*, 7:147-153 (2011).

Dechsiri, C., Fluidization with Vibrating Baffles, *Particle Transport in Fluidized Beds: Experiments and Stochastic Models* s.n., University of Groningen, Chapter 8, pp. 151-165 (2004).

McPherson, A., "Introduction to protein crystallization," *Methods*, Science Direct, Elsevier, 34:254-265 (2004).

Meier, S. and Duus, J., "Carbohydrate dynamics: antibody glycans wiggle and jiggle," *Nat Chem Biol*, 7:131-132 (2011).

Shah, B. et al., "Analytical techniques for quantification of amorphous/crystalline phases in pharmaceutical solids," *J Pharmaceutical Sci*, 95(8):1641-1665 (2006).

Zang, Y. et al., "Towards protein crystallization as a process step in downstream processing of therapeutic antibodies: screening and optimization at microbatch scale," *PLOS-One*, 6(9):e25282 (2011).

* cited by examiner

Recipes

Application Type: Concentrate - Wash - Harvest    Mix Bed: 240   Mix and Harvest Speed: 1000 (g)

Recipe Name: test2

Speed: 1000 (g) Bioreactor Volume: 1.0 (L)    (mL/min/Ch) for: 0.0 sec, 0 Cycles FWD Bioreactor Prime Volume: 1.0 (mL)    Harvest Flow Rate: 300 (mL/min) /Ch

Disabled Cycle Volume: 1.00 (L) /Ch    Initial Dump Volume: 1 (mL)

Establish Bed: 80 (mL/min) /Ch for: 1.00 (min)    Harvest Volume: 1 (mL)

Flow Rate Ramp Time: 1.00 (min)

Normal Flow Rate: 400 (mL/min) /Ch    Valve Set: NORMAL

Recirc Wash: 0 (mL) Recirc for: 0.00 (min), 0 Cycles

Cycle Volume Calculations

Bioreactor Cell Density: 1.00   Million Cells / mL
Cell Diameter: 0   um
Chamber Capacity: 20.00   Billion Cells
Fill: 80.00   %

Wash: 350 (mL/min) /Ch for: 1.00 (#) /Ch
2nd Wash: 350 (mL/min) / Ch for: 1.00 (#) /Ch Wash 1 used for Buffer Exchange:   ne: 16.00   es: 0.02   L / Ch   Cycles   LOAD Wash 2 used for Concentration:
rrent Estimates
es: 0.25 Cycles (Will Round up)
ne: 2.8 L
Harvest Volume: 0.0 L
Waste Volume: 3.20L Active Vessels: A B C D

| 1 | 2 | 3 | 4 | 5 | 6 | 7 | 8 | 9 | 10 |

FIGURE 3

METHODS DIRECTED TO CRYSTALLINE BIOMOLECULES

CROSS-REFERENCE TO RELATED APPLICATIONS

This application claims priority to U.S. Provisional Patent Application No. 62/471,358, filed on Mar. 14, 2017, and U.S. Provisional Patent Application No. 62/476,359, filed on Mar. 24, 2017, the contents of each application are incorporated herein by reference.

BACKGROUND

Antibodies constitute powerful therapeutic agents characterized by limited side effects due to their ability to specifically target a distinct antigen on a cell, bacteria, virus, or toxin. In 1986, the first therapeutic monoclonal antibody, Orthoclone OKT3, was introduced into the market. Since then, this class of biopharmaceutical products has significantly grown. In late 2014, 47 monoclonal antibody products had received approval in the U.S. or Europe for the treatment of a variety of diseases, including cancer and inflammatory, cardiovascular, respiratory, and infectious diseases. Given the current approval rate of about four products per year, it is estimated that approximately 70 monoclonal antibody products will be commercially available by 2020. See, Ecker et al., MAbs 7(1): 9-14 (2015).

Though it is reported that the projected antibody market in the United States is anticipated to increase to over $10 billion, the production of such therapeutics is not without limitations. One disadvantage of therapeutic antibodies is the cost of downstream processing to achieve the required high purity levels. While greater than 90% purity levels can be achieved via Protein A chromatography, the cost of the adsorption media is a major drawback. Another limiting factor of therapeutic antibodies is the sensitivity of antibody structure to chemical and physical denaturation encountered during delivery and storage. Even though researchers have developed approaches to improve stability of antibody formulations, some of these methods lead to a loss of protein activity and/or cost more due to the additional expense of protein stabilizing carriers or formulations.

Protein crystallization is recognized in principle as an effective and scalable method of protein purification. Crystalline proteins offer higher stability relative to their protein solution counterparts and thus have longer shelf lives. Protein purification through crystallization has been shown feasible by test protein products, including ovalbumin and a lipase. Insulin is the only therapeutic protein crystallized at industrial scale. Crystallization of antibodies is not yet routine, due to complications in their phase behavior. Precipitation, phase separation, and the formation of gel-like phases can occur and "kinetically trap the system far from equilibrium and as a consequence reduce the yield of crystalline protein or inhibit crystal formation completely." See, Zang et al., PLOS One 6(9): e25282 (2011). Conventional purification techniques such as tangential flow and alternating flow filtration are not suitable for protein crystallization purification because of membrane fouling (i.e., the crystals clog the pores of the filter medium). Also, the high pressure required to maintain flow through the filter can lead to excessive shear, breakage, and compaction of crystals. When the protein is an antibody, these issues are exacerbated because the crystals of such proteins are sticky and fragile.

Thus, there is a need in the art for efficient methods of preparing compositions comprising crystalline antibodies.

SUMMARY

Disclosed herein are methods of preparing a composition comprising crystalline biomolecules, for example, antigen-binding biomolecules, including, but not limited to, antibodies or immunoglobulins, antigen-binding fragments thereof, and the like. In exemplary embodiments, the method comprises using a counter-flow gradient centrifuge (CFGC) for exchanging the solution (e.g., buffer) in which the crystalline biomolecules reside and/or for concentrating the solution (e.g., buffer) comprising the crystalline biomolecules. The disclosed methods are advantageous, because the steps occur in a low-shear, closed system, and under aseptic processing conditions. Multiple steps are performed in the same apparatus, thereby preventing loss of product upon transfer to different apparatuses. Due to the low-shear environment maintained throughout the methods described herein, the crystalline biomolecules remain separated from one another, thereby minimizing the formation of aggregates. The disclosed methods lead to attainment of a homogenous crystal slurry that can be readily pumped into downstream processing operations, such as filling.

In exemplary embodiments, the method of preparing a composition comprising crystalline biomolecules comprises forming a fluidized bed of crystalline biomolecules in a rotating chamber comprising an inlet and an outlet. Without being bound to a particular theory, it is believed that the fluidized bed is created by rotating the chamber about a substantially horizontal axis to create a centrifugal force ($F_{centrifugal}$) in said chamber, flowing a first stream of a first solution through the inlet in a direction opposite to the direction of the $F_{centrifugal}$ and at a first flow rate (FR1) having a force ($F_{FR1}$) which counter balances $F_{centrifugal}$, and collecting the first solution from the chamber while substantially maintaining the formation of the fluidized bed of crystallized biomolecules.

In exemplary embodiments, the method also comprises replacing the first stream of the first solution with a second stream of a second solution while substantially maintaining the formation of the fluidized bed of crystallized biomolecules. In exemplary aspects, the method comprises flowing a second stream of a second solution to replace the first stream of the first solution while substantially maintaining the formation of the fluidized bed of crystallized biomolecules. In exemplary aspects, the method comprises flowing a second stream of a second solution through the inlet in a direction opposite to the direction of the $F_{centrifugal}$ and at a flow rate (FR) equivalent to FR1 having a force (F) equal to $F_{FR1}$, such that the force of the second stream counter balances $F_{centrifugal}$, and collecting the second solution from the chamber while substantially maintaining the formation of the fluidized bed of crystallized biomolecules.

In exemplary embodiments, the method alternatively or additionally comprises concentrating the crystallized biomolecules within a region of the chamber by changing FR1 to a second flow rate (FR2) having a force ($F_{FR2}$) which is less than $F_{centrifugal}$ or by increasing the speed of rotation of the chamber to increase $F_{centrifugal}$ to a level which is greater than $F_{FR1}$.

In exemplary aspects, the method comprises removing the crystalline biomolecules from the chamber by, e.g., flowing a second stream into the chamber through the outlet in a direction which is parallel to the direction of the $F_{centrifugal}$.

Also disclosed herein are methods of detecting crystalline biomolecules and/or amorphous biomolecules in a sample. In exemplary embodiments, the method comprises obtaining a plurality of $^1$H NMR Carr-Purcell-Meiboom-Gill (CPMG) spectra of the sample, and obtaining $^{13}$C NMR cross-polarization (CP) spectra of the sample.

BRIEF DESCRIPTION OF THE DRAWINGS

FIG. 3 is a picture of a kSep® Concentrate-Wash-Harvest (CWH) graphical user interface.

DETAILED DESCRIPTION

Figure 1:
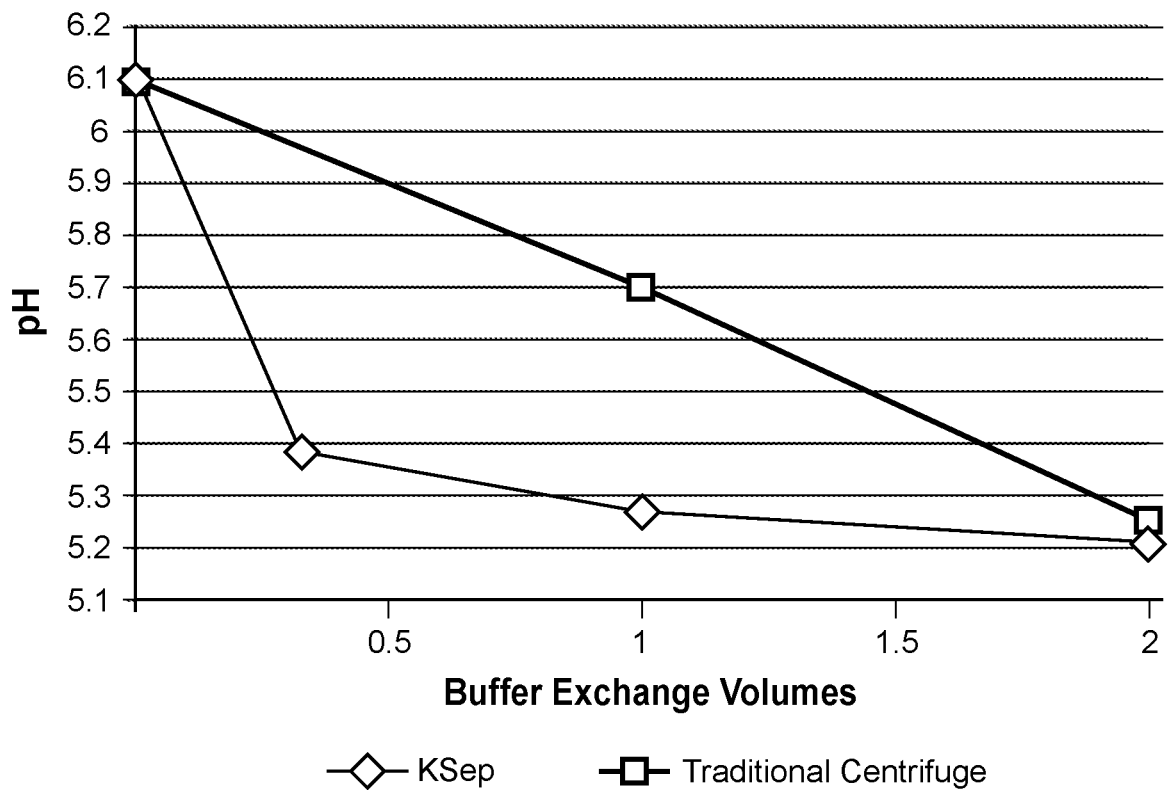
FIG. 1 is a graph of the outlet pH profile for kSep® and a traditional centrifuge.

Disclosed herein are methods directed to crystalline biomolecules. Provided are methods for preparing a composition comprising crystalline biomolecules. In exemplary embodiments, the method comprises forming a fluidized bed of crystalline biomolecules in a rotating chamber comprising an inlet and an outlet, wherein the fluidized bed is created by rotating the chamber about a substantially horizontal axis to create a centrifugal force ($F_{centrifugal}$) in said chamber, flowing a first stream of a first solution through the inlet in a direction opposite to the direction of the $F_{centrifugal}$ and at a first flow rate (FR1) having a force ($F_{FR1}$) which counterbalances $F_{centrifugal}$, and collecting the first solution from the chamber while substantially maintaining the formation of the fluidized bed of crystallized biomolecules.

In exemplary embodiments, the method comprises a buffer exchange step, a concentration step, or both a buffer exchange step and a concentration step. Further description of each step is provided below.

Buffer Exchange Step

In exemplary embodiments, the method comprises a buffer exchange step and, in exemplary aspects, such step occurs while maintaining the fluidized bed of crystalline biomolecules. In exemplary aspects, the method comprises replacing the first stream of the first solution with a second stream of a second solution while substantially maintaining the formation of the fluidized bed of crystallized biomolecules. In exemplary aspects, the method comprises flowing a second stream of a second solution to replace the first stream of the first solution while substantially maintaining the formation of the fluidized bed of crystallized biomolecules.

In exemplary aspects, the method comprises flowing a second stream or a second solution through the inlet in a direction opposite to the direction of the $F_{centrifugal}$ and at a flow rate (FR) equivalent to FR1 having a force (F) equal to $F_{FR1}$, such that the force of the second stream counterbalances $F_{centrifugal}$, and collecting the second solution from the chamber while substantially maintaining the formation of the fluidized bed of crystallized biomolecules. In exemplary aspects, $F_{centrifugal}$ is suitable to maintain the crystalline biomolecules in the fluidized bed. In certain aspects, $F_{centrifugal}$ is in the range of about 500 g to about 3000 g. In certain aspects, $F_{centrifugal}$ is in the range of about 750 g to about 1250 g. In certain aspects, $F_{centrifugal}$ is about 1000 g (±100 g) during this step.

The feed volume of the second stream of the second solution is sufficient to maintain the crystalline biomolecules in the fluidized bed. In exemplary aspects, the feed volume of the second stream of the second solution is about 50 to 500 ml. In exemplary aspects, the feed volume of the second stream of the second solution is about 100 to 300 ml. In exemplary aspects, the number of volumes of the first solution per chamber is 2 or more. In exemplary aspects, FR1 is sufficient to maintain the crystalline molecules in the fluidized bed. In exemplary aspects, FR1 is about 50 ml/min to about 150 ml/min. In exemplary aspects, FR1 is about 70 ml/min to about 120 ml/min.

Advantageously, the methods are not limited to a particular type of buffer, provided that the buffer does not negatively impact the integrity of the crystalline biomolecules, e.g., the buffer does not negatively impact the size, shape and/or product quality of the crystalline biomolecules. In this regard, each of the first solution and second solution can be any type of buffer or solution characterized by any pH. In exemplary aspects, the pH of the solution is a physiological pH, e.g., 6.5 to 7.5. In exemplary aspects, the solution can have a pH that is at least 5, at least 5.5, at least 6, at least 6.5, at least 7, at least 7.5, at least 8, at least 8.5, at least 9, at least 9.5, at least 10, or at least 10.5 up to and including pH 11. In exemplary aspects, one or both of the first solution and second solution independently comprise a buffering agent. In exemplary aspects, the buffering agent is selected from the group consisting of: phosphate buffers (e.g., PBS), triethanolamine, Tris, bicine, TAPS, tricine, HEPES, TES, MOPS, PIPES, cacodylate, MES, acetate, citrate, succinate, histidine or other pharmaceutically acceptable buffers.

In exemplary aspects, the first solution is a hypertonic protein crystallization buffer. In exemplary aspects, the second solution is a formulation buffer which is safe for administration to a mammal, e.g., a human. In exemplary aspects, the second solution has a physiological pH and is sterile.

Concentration Step

In additional or alternative embodiments, the method comprises concentrating the crystallized biomolecules within a region of the chamber. In exemplary aspects, the method comprises concentrating the crystallized biomolecules after a buffer exchange step, such as, e.g., any of those described herein. In exemplary aspects, the concentrating step occurs by either (i) changing FR1 to a second flow rate (FR2) having a force ($F_{FR2}$) which is less than $F_{centrifugal}$ or (ii) by increasing the speed of rotation of the chamber to increase $F_{centrifugal}$ to a level which is greater than $F_{FR1}$, or (iii) both (i) and (ii). In exemplary aspects, $F_{centrifugal}$ is 1000 g during at least this step. In exemplary aspects, the feed volume of the second stream of the second solution is about 100 to 500 ml. In exemplary aspects, the feed volume of the second stream of the second solution is about 150 ml to about 350 ml, e.g., about 150 ml, about 200 ml, about 250 ml, about 300 ml, or about 350 ml. In exemplary aspects, the number of volumes of the first solution per chamber is 1. In exemplary aspects, FR2 is about 10 ml/min to about 50 ml/min. In exemplary aspects, FR2 is less than about 60 ml/min. In exemplary aspects, FR2 is about 10 ml/min to about 50 ml/min. In exemplary aspects, FR2 is about 20 ml/min to about 40 ml/min. In exemplary aspects, FR2 is about 20 ml/min, about 25 ml/min, about 30 ml/min, about 35 ml/min, or about 40 ml/min.

In exemplary aspects, after the concentrating step, the concentration of the crystalline biomolecules is increased at least 2-fold, at least 3-fold, or at least 4-fold.

Harvest Step

In exemplary aspects, the method comprises removing the crystalline biomolecules from the chamber. In exemplary aspects, the method comprises removing the crystalline biomolecules from the chamber after concentrating the crystalline biomolecules within a region of the chamber. In exemplary aspects, the method comprises removing a concentrated suspension of the crystalline biomolecules from the chamber slowly without disrupting the packed crystal suspension and/or without causing cavitation within the packed crystal suspension. Cavitation within the packed crystal suspension is undesirable as it disrupts the concentration profile and creates a non-uniform concentration gradient across the concentrated crystal suspension.

In exemplary aspects, the method comprises flowing a second stream into the chamber through the outlet in a direction which is parallel to the direction of the $F_{centrifugal}$ to remove the crystalline biomolecules from the chamber.

In exemplary aspects, the method comprises decreasing $F_{centrifugal}$ to a level of about 5 g to about 20 g or to a level of about 5 g to about 15 g. In exemplary aspects, $F_{centrifugal}$ is decreased to below about 10 g, e.g., about 8 g.

In exemplary aspects, FR1 is controlled by a first pump and the first pump is set to about 10 ml/min to about 100 ml/min after the buffer exchange and/or concentrating step. In exemplary aspects, FR1 is controlled by a first pump and the first pump is set to less than about 75 ml/min. In exemplary aspects, FR1 is controlled by a first pump and the first pump is set to about 15 ml/min to about 65 ml/min after the buffer exchange and/or concentrating step. In exemplary aspects, the first pump is set to about 45 ml/min to about 65 ml/min, optionally, about 50 ml/min.

In exemplary aspects, the rotating chamber is connected to a chamber peristaltic pump. In exemplary instances, the chamber peristaltic pump is pumping in the same direction of the first pump and $F_{centrifugal}$. Without being bound to a particular theory, the first pump acts as a "pulling" mechanism that sucks the material out of the chamber, whereas the chamber peristaltic pump acts as a "pushing" mechanism to ensure there is no cavitation of the biomolecule. In exemplary aspects, the chamber peristaltic pump is set to about 50 ml/min to about 150 ml/min after the buffer exchange and/or concentrating step. In exemplary aspects, the chamber peristaltic pump is set to less than 100 ml/min. In some embodiments, the chamber peristaltic pump is set to about 60 ml/min to about 90 ml/min. In exemplary instances, the chamber peristaltic pump is set to about 75 ml/min, the first pump is set to about 50 ml/min, and $F_{centrifugal}$ is decreased to below 10 g, optionally 8 g.

CFGC Apparatus

In exemplary aspects, the disclosed methods are carried out in a counterflow gradient centrifugation (CFGC) system. In exemplary aspects, the apparatus comprises more than one rotating chamber. In exemplary aspects, the apparatus comprises at least 2, at least 4 or at least 6 rotating chambers. In exemplary aspects, the apparatus comprises 4 or 6 chambers. In exemplary embodiments, the method is carried out in an apparatus comprising more than one rotating chamber and each chamber can be operated simultaneously with other chambers of the apparatus, or can be operated on its own. In exemplary aspects, the steps of the disclosed method are carried out in more than one chamber. In exemplary aspects, the steps of the disclosed method are carried out in two, three, or four chambers. In exemplary aspects, the steps of the disclosed method are carried out in five or six chambers. In exemplary aspects, the steps of the disclosed method are carried out in more than about 6, more than about 10, more than about 20 chambers.

In exemplary aspects, the apparatus is a kSep® system. In exemplary aspects, the apparatus is a kSep®400, which has four individual chambers, each of which has a 100-ml capacity. In exemplary aspects, the apparatus is a kSep®6000S, which has six individual chambers, each of which has a 1000-ml capacity. The kSep®6000S has a maximum flowrate of 720 L/hr.

In exemplary aspects, when the disclosed method is carried out in more than one chamber of the apparatus, the crystalline biomolecules are removed from the chambers one at a time. For example, the crystalline biomolecules are removed from each chamber in a sequential manner. Thus, the removal of crystalline biomolecules from one chamber of the apparatus occurs at a time distinct from when crystalline biomolecules are removed from another chamber of the apparatus. Without being bound to a particular theory, it is believed that removing crystalline biomolecules from one chamber at a time reduces the chances of cavitation of the crystalline biomolecules.

Exemplary Embodiments

In exemplary aspects, the method of preparing a composition comprising crystalline biomolecules comprises (a) forming a fluidized bed of crystalline biomolecules in a rotating chamber comprising an inlet and an outlet, wherein the fluidized bed is created by rotating the chamber about a substantially horizontal axis to create a centrifugal force ($F_{centrifugal}$) in said chamber, flowing a first stream of a first solution through the inlet in a direction opposite to the direction of the $F_{centrifugal}$ and at a first flow rate (FR1) having a force ($F_{FR1}$) which counter balances $F_{centrifugal}$, and collecting the first solution from the chamber while substantially maintaining the formation of the fluidized bed of crystallized biomolecules, (b) performing step (i), step (ii), or step (iii), wherein step (i) is flowing a second stream of a second solution to replace the first stream of the first solution while substantially maintaining the formation of the fluidized bed of crystallized biomolecules, step (ii) is concentrating the crystallized biomolecules within a region of the chamber by changing FR1 to a second flow rate (FR2) having a force ($F_{FR2}$) which is less than $F_{centrifugal}$ or by increasing the speed of rotation of the chamber to increase $F_{centrifugal}$ to a level which is greater than $F_{FR1}$, and step (iii) is a combination of step (i) and step (ii), and (c) removing the crystalline biomolecules from the chamber. In exemplary aspects, the crystalline biomolecules are removed from the chamber by flowing a second stream into the chamber through the outlet in a direction which is parallel to the direction of the $F_{centrifugal}$ to remove the crystalline biomolecules from the chamber.

Additional Steps

The methods disclosed herein can comprise additional steps. For example, the methods can comprise one or more upstream steps or downstream steps involved in producing, purifying, and formulating a recombinant protein. In exemplary embodiments, the method comprises steps for generating host cells that express a recombinant protein (e.g., recombinant antibody). The host cells can be prokaryotic host cells, e.g., *E. coli* or *Bacillus subtilis*, or the host cells can be eukaryotic, e.g., yeast cells, filamentous fungi cells, protozoa cells, insect cells, or mammalian cells (e.g., CHO cells). Such host cells are described in the art. See, e.g., Frenzel, et al., *Front Immunol* 4: 217 (2013). For example, the methods comprise, in some instances, introducing into host cells a vector comprising a nucleic acid comprising a nucleotide sequence encoding the recombinant protein, or a polypeptide chain thereof.

In exemplary embodiments, the method comprises steps for culturing host cells expressing a recombinant protein (e.g., recombinant antibody). Such steps are known in the art. See, e.g., Li et al., *MAbs* 2(5): 466-477 (2010).

In exemplary embodiments, the method comprises steps for purifying the recombinant protein (e.g., recombinant antibody) from the culture. In exemplary aspects, the method comprises one or more chromatography steps, e.g., affinity chromatography (e.g., protein A affinity chromatography), ion exchange chromatography, and/or hydrophobic interaction chromatography. In exemplary aspects, the method comprises steps for producing crystalline biomolecules from a solution comprising the recombinant proteins. In exemplary aspects, the method comprises steps for preparing crystalline material, including those described in International Patent Application Publication No. WO2016010927, entitled "CRYSTALLINE ANTIBODY FORMULATIONS" which is incorporated by reference in its entirety. The method can comprise in some aspects controlling the solution conditions or factors which affect crystallization, e.g., the rate of evaporation of solvent, organic solvents or additives, the presence of appropriate co-solutes and buffers, pH, and temperature. A comprehensive review of the various factors affecting the crystallization of proteins has been published by McPherson (1985, Methods Enzymol 114: 112-120). For guidance, the teachings of McPherson and Gilliland (1988, J Crystal Growth, 90: 51-59) including comprehensive lists of polypeptides that have been crystallized, as well as the conditions under which they were crystallized, is available. Additionally, a compendium of crystals and crystallization recipes, as well as a repository of coordinates of solved protein structures, is maintained by the Protein Data Bank at the Brookhaven National Laboratory (www.rcsb.org/pdb/; Bernstein et al., 1977, J Mol Biol 112: 535-542). In general, crystals are produced by combining the polypeptide (i.e., antibody) to be crystallized with an appropriate aqueous solvent or aqueous solvent containing appropriate crystallization agents, such as salts or organic solvents or additives (collectively the "crystallization reagent"). The solvent is combined with the polypeptide and can be subjected to agitation at a temperature determined experimentally to be appropriate for the induction of crystallization and acceptable for the maintenance of polypeptide activity and stability. Laboratory-scale methods for crystallization include hanging drop vapor diffusion, sitting drop vapor diffusion, microdialysis, microbatch, under oil, in gel and sandwich drop methods. The solvent can optionally include co-crystallization additives, such as precipitants, fatty acids, reducing agents, glycerol, sulfobetaine, surfactants, polyols, divalent cations, co-factors, or chaotropes, and amino acids as well as buffer species to control pH. "Co-crystallization additives" include compounds that facilitate crystallization of a polypeptide and/or compounds that stabilize the protein and protect against denaturation. Examples of co-solutes include ammonium acetate, ammonium chloride, ammonium fluoride, ammonium formate, ammonium nitrate, ammonium phosphate, ammonium sulfate, cadmium chloride, cadmium sulfate, calcium acetate, calcium chloride, cesium chloride, cobaltous chloride, $CH3(CH_2)_{15}N(CH_3)_3$ Br.-(CTAB), di-ammonium citrate, di-ammonium hydrogen phosphate, di-ammonium phosphate, di-ammonium tartrate, di-potassium phosphate, di-sodium phosphate, di-sodium tartrate, DL-malic acid, ferric chloride, L-proline, lithium acetate, lithium chloride, lithium nitrate, lithium sulfate, magnesium acetate, magnesium chloride, magnesium formate, magnesium nitrate, magnesium sulfate, nickel chloride, potassium acetate, potassium bromide, potassium chloride, potassium citrate, potassium fluoride, potassium formate, potassium nitrate, potassium phosphate, potassium sodium tartrate, potassium sulfate, potassium thiocyanate, sodium acetate, sodium bromide, sodium chloride, sodium citrate, sodium fluoride, sodium formate, sodium malonate, sodium nitrate, sodium phosphate, sodium sulfate, sodium thiocyanate, succinic acid, tacsimate, tri-ammonium citrate, tri-lithium citrate, trimethylamine N-oxide, tri-potassium citrate, tri-sodium citrate, zinc acetate, zinc sulfate, and other compounds that function to supply co-solutes. "Crystallization" include compounds that maintain the pH of a solution in a desired range to facilitate crystallization of a polypeptide. Examples include ACES (N-(2-acetamido)-2-aminoethanesulfonic acid), BES (N,N-bis(2-hydroxyethyl)-2-aminoethanesulfonic acid), Bicine (N,N-Bis(2-hydroxyethyl)glycine), BIS-TRIS (2,2-bis-(hydroxymethyl)-2,2',2"-nitrilotriethanol), boric acid, CAPS (3-[cyclohexylamino]-1-propanesulfonic acid), citric acid, EPPS (HEPPS, 4-(2-Hydroxyethyl)piperazine-1-propanesulfonic acid), Gly-Gly ($NH_2CH_2CONHCH_2COOH$, glycyl-glycine), HEPES (4-(2-hydroxyethyl)piperazine-1-ethanesulfonic acid), imidazole, MES (2-morpholinoethanesulfonic acid), MOPS (3-(N-morpholino)-propanesulfonic acid), PIPES (piperazine-1,4-bis(2-ethanesulfonic acid)), potassium chloride, sodium acetate, sodium bicarbonate, sodium phosphate monobasic (sodium dihydrogen phosphate), sodium phosphate dibasic, TAPS(N-[tris-(hydroxymethyl)methyl]-3-aminopropanesulfonic acid), TAPSO(N-[tris(hydroxymethyl)methyl]-3-amino-2-hydroxypropanesulfonic acid), TES (N-[tris(hydroxymethyl)methyl]-2-aminoethanesulfonic acid), Tricine (N-[tris(hydroxymethyl)methyl]glycine), Tris-HCl, TRIZMA (2-amino-2-(hydroxymethyl)-1,3-propanediol), and other compounds that function to maintain a solution at or near a specified pH.

The selection of precipitants are one factor affecting crystallization. For example, PEG products, e.g. of molecular weight 200 to 20,000 kD, can be used. PEG3350 is a long polymer precipitant or dehydrant which works by volume exclusion effect. Lyotropic salts, such as ammonium sulfate, promote precipitation processes, as do short-chain fatty acids, such as caprylic acid. Polyionic species also are useful precipitants.

Antibodies for use in formulations for subcutaneous injection, for example, preferably are precipitated at a physiologic pH range and in a crystallization reagent that provides isotonic osmolality. The need for additives, co-solutes, buffers, etc. and their concentrations are determined experimentally to facilitate crystallization.

In an industrial-scale process, controlled precipitation leading to crystallization can best be carried out by the simple combination of polypeptide, precipitant, co-solutes and, optionally, buffers in a batch process. As another option, polypeptides can be crystallized by using polypeptide precipitates as the starting material ("seeding"). In this case, polypeptide precipitates are added to a crystallization solution and incubated until crystals form.

Alternative laboratory crystallization methods, such as dialysis or vapor diffusion, can also be adopted. McPherson, supra and Gilliland, supra, include a comprehensive list of suitable conditions in their reviews of the crystallization literature. Occasionally, in cases in which the crystallized polypeptide is to be crosslinked, incompatibility between an intended crosslinking agent and the crystallization medium might require exchanging the crystals into a more suitable solvent system.

According to some embodiments, polypeptide crystals, crystal formulations and compositions are prepared by the following process: first, the polypeptide is crystallized. Next, excipients or ingredients as described herein are added directly to the mother liquor. Alternatively, the crystals are suspended in a solution of excipient or other formulary ingredients, after the mother liquor is removed, for a minimum of 1 hour to a maximum of 24 hours. The excipient concentration is typically between about 0.01 to 30% w/w, which corresponds to a polypeptide crystal concentration of 99.99 to 70% w/w, respectively. In one embodiment, the excipient concentration is between about 0.1 to 10%, which corresponds to a crystal concentration of 99.9 to 90% w/w, respectively. The mother liquor can be removed from the crystal slurry either by filtration, buffer exchange, or by centrifugation.

Subsequently, the crystals are washed with any isotonic injectable vehicle as long as the these vehicles do not dissolve the crystals, optionally with solutions of 50 to 100% of one or more organic solvents or additives such as, for example, ethanol, methanol, isopropanol or ethyl acetate, or polyethelene glycol (PEG), either at room temperature or at temperatures between −20° C. to 25° C. In addition, water can be used to wash the crystals. The crystals are the dried either by passing a stream of nitrogen, air, or inert gas over the crystals. Finally, micronizing of the crystals can be performed if necessary. The drying of polypeptide crystals is the removal of water, organic solvent or additive, or liquid polymer by means including drying with $N_2$, air, or inert gases; vacuum oven drying; lyophilization; washing with a volatile organic solvent or additive followed by evaporation of the solvent; or evaporation in a fume hood. Typically, drying is achieved when the crystals become a free-flowing powder. Drying can be carried out by passing a stream of gas over wet crystals. The gas can be selected from the group consisting of: nitrogen, argon, helium, carbon dioxide, air or combinations thereof. The diameter of the particles achieved can be in the range of 0.1 to 100 micrometers, or in the range of 0.2 to 10 micrometers, or in the range of 10 to 50 micrometers, or in the range of 0.5 to 2 micrometers. For formulations to be administered by inhalation, in one embodiment the particles formed from the polypeptide crystals are in the range of 0.5 to 1 micrometers.

According to some embodiments, when preparing protein crystals, protein crystal formulations or compositions, enhancers, such as surfactants are not added during crystallization. According to some other embodiments, when preparing protein crystals, protein crystal formulations or compositions, enhancers, such as surfactants are added during crystallization. Excipients or ingredients are added to the mother liquor after crystallization, at a concentration of between about 1-10% w/w, alternatively at a concentration of between about 0.1-25% w/w, alternatively at a concentration of between about 0.1-50% w/w. These concentrations correspond to crystal concentrations of 99-90% w/w, 99.9-75% w/w and 99.9-50% w/w, respectively. The excipient or ingredient is incubated with the crystals in the mother liquor for about 0.1-3 hrs, alternatively the incubation is carried out for 0.1-12 hrs, alternatively the incubation is carried out for 0.1-24 hrs.

In some or any embodiments, the ingredient or excipient is dissolved in a solution other than the mother liquor, and the protein crystals are removed from the mother liquor and suspended in the excipient or ingredient solution. In some embodiments, the excipient or ingredient solution (or resuspension vehicle) is a mixture of excipients or ingredients or surfactants that is isotonic and injectable. In some embodiments, the excipient or ingredient solution (or resuspension vehicle) is not a mixture of excipients or ingredients or surfactants that is isotonic and injectable. The ingredient or excipient concentrations and the incubation times are the same as those described above.

In exemplary embodiments, the method comprises steps for formulating the purified biomolecule (e.g., antibody). Exemplary steps are described in Formulation and Process Development Strategies for Manufacturing, eds. Jameel and Hershenson, John Wiley & Sons, Inc. (Hoboken, NJ), 2010.

In exemplary embodiments, the method comprises analyzing the sample for crystalline vs. amorphous forms of the biomolecule. In exemplary aspects, the method comprises quantitative analysis of the sample.

Biomolecules

As used herein, the term "biomolecule" or "biological molecule" refers to a large macromolecule that is present in living organisms or can be made or metabolized by a living organism, or is structurally based on a molecule present in or made or metabolized by living organisms. Biomolecules include, but are not limited to being, polypeptides, proteins, polysaccharides, lipids (e.g., glycolipids, phospholipids, sterols), and polynucleotides or nucleic acids (e.g., DNA or RNA).

The methods disclosed herein are not limited to any particular type of biomolecule so long as the biomolecule can assume a crystalline form. In exemplary aspects, the crystalline biomolecule is a protein comprising one or more polypeptide chains. In exemplary aspects, the crystalline protein is a hormone, growth factor, cytokine, a cell surface receptor, or any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.).

In exemplary instances, the biomolecule is an antibody or immunoglobulin, or a fragment thereof, e.g., an antigen-binding antibody fragment. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4$^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the invention include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

The antibody may be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. In certain aspects, the biomolecule is an antibody, such as a human antibody. In certain aspects, the biomolecule is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In exemplary aspects, the biomolecule can be an antibody fragment, e.g., a Fab, Fc, F(ab')$_2$, or a pFc', that retains at least one glycosylation site.

The architecture of antibodies has been exploited to create a growing range of alternative antibody formats that spans a molecular-weight range of at least about 12-150 kDa and has a valency (n) range from monomeric (n=1), to dimeric (n=2) and to trimeric (n=3) to tetrameric (n=4) and potentially higher; such alternative antibody formats are referred to herein as "antibody protein products".

Antibody protein products include those based on antibody fragments, e.g., scFvs, Fabs and VHH/VH (discussed below), which retain full antigen-binding capacity. The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

In exemplary aspects, the biomolecule comprises any one of these antibody protein products. In exemplary aspects, the biomolecule is any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate.

The biomolecule may be an antibody protein product in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Methods of Detecting Crystalline and Amorphous Biomolecules

To ensure a robust and safe formulation, the extent of crystallinity or disorder is optionally monitored during various processing steps (e.g., bulk material scale-up, formulation development, manufacturing), and throughout the shelf-life of a pharmaceutical product. Amorphous forms of pharmaceutical drug substances along with their downstream consequences in drug products and biological systems is well documented. See, e.g., Shah et al., J Pharm Sci 95(8): 1641 (2006). An amorphous solid is usually defined in reference to a crystalline solid and typically lacks long-range translational orientation symmetry that is characteristic of crystalline structures. The amorphous phase can occur throughout the particle or in parts of the particle, such as the particle's surface. Detection of amorphous forms of a solid can be challenging, as the disorder can be too small to easily detect. Sufficiently large amounts of disorder can cause changes in product performance, affecting, e.g., post-compression hardness, enhanced dissolution rate, reduced chemical stability, and moisture-induced recrystallization during storage. See, Shah et al., 2006, supra. Various quantification techniques exist to detect amorphous forms of a solid (relative to a crystalline solid), and include, e.g., powder X-ray diffraction (PXRD), differential scanning calorimetry (DSC), isothermal microcalorimetry (IMC), solution calorimetry (SC), infrared spectroscopy (IRR, Fourier-Transform (FT) Raman Spectroscopy, and solid-state NMR (ssNMR). However, each has one or more disadvantages.

In addition to the methods of preparing a composition comprising crystalline biomolecules, provided herein are efficient and facile methods for detecting crystalline biomolecules and/or amorphous biomolecules in a sample.

In exemplary embodiments, the method of detecting crystalline biomolecules and/or amorphous biomolecules in a sample comprises performing high resolution ssNMR (solid state Nuclear Magnetic Resonance) analysis on the sample. In exemplary embodiments, the method comprises obtaining high resolution $^{13}$C ssNMR spectra using proton decoupling and magic angle spinning (MAS), wherein sensitivity enhancement is achieved by cross-polarization (CP). In exemplary aspects, the method of detecting crystalline biomolecules and/or amorphous biomolecules in a sample comprises obtaining a plurality of $^1$H Carr-Purcell-Meiboom-Gill (CPMG) spectra of the sample and obtaining a $^{13}$C cross-polarization (CP) spectra of the sample. In exemplary aspects, the method comprises operating a $^1$H resonance frequency of about 250 to about 1000 MHz (optionally, about 500 MHz, about 700 MHz, about 800 MHz, about 900 MHz). In exemplary aspects, the method comprises maintaining the temperature at about 250 to 350 K, e.g., about 250 K, about 275 K, about 300 K, about 325 K, or about 350 K. In exemplary aspects, the method comprises operating a magic angle spinning (MAS) probe. In exemplary instances, the method comprises operating a MAS probe comprising at least two radio frequency (rf) channels. In exemplary aspects, the MAS probe is tuned to $^1$H and $^{13}$C. In certain aspects, the MAS probe is operated with a spinning frequency of about 2 kHz to about 8 kHz, or about 3 kHz to about 5 kHz, e.g., about 4 kHz. In some aspects, the method comprises using 90 degree pulses, e.g., $^1$H 90 degree pulses about 2.5 µs. In some aspects, the $^1$H CPMG spectra are obtained with about 5 to about 100 pi pulses (e.g., about 10 to about 90, about 20 to about 80 pi pulses) of about 2 µs to about 20 µs (e.g., about 5 µs, about 10 µs, about 15 µs, about 20 µs) in length. For example, each of the pi pulses can be separated by 500 µs, and optionally, the total time of CPMG pulses is 10 ms. In exemplary aspects, the method comprises obtaining a plurality of $^1$H CPMG spectra while spinning at a frequency of up to 5 kHz, above 8 kHz, or about 14 kHz. In some aspects, the contact time of the $^{13}$C CP during the measuring is about 100 µs to about 10 ms, e.g., about 250 µs, about 500 µs, about 750 µs, about 1 ms, about 2 ms, about 3 ms, about 4 ms, about 5 ms, about 6 ms, about 7 ms, about 8 ms, about 9 ms, about 10 ms). In exemplary aspects, the measuring comprised an RF spin lock pulse on $^{13}$C of about 20 kHz to about 100 kHz, e.g., about 50 kHz. In exemplary aspects, the ramp pulse on $^1$H is matched.

The method of detecting in exemplary embodiments in some aspects comprises quantifying the content of crystalline biomolecules in the sample. In exemplary instances, the crystalline biomolecules exhibit a spectroscopic signature different than amorphous biomolecules. In exemplary instances, the crystalline biomolecules exhibit a spectroscopic signature of higher molecular mobility than amorphous biomolecules.

Accordingly, provided herein are methods of quantifying the content of crystalline biomolecules and/or amorphous biomolecules in a sample. In exemplary aspects, the method comprises: (A) obtaining a plurality of $^1$H NMR Carr-Purcell-Meiboom-Gill (CPMG) spectra of the sample, and (B) obtaining a $^{13}$C NMR cross-polarization (CP) spectra of the sample. The method of quantifying the content disclosed herein can be carried out according to the teachings in reference to methods of detecting crystalline biomolecules and/or amorphous biomolecules in a sample.

In exemplary aspects of the methods of detecting or quantifying, the crystalline biomolecules are bi-refringant and optionally, do not diffract. In exemplary aspects, the crystalline biomolecules do not diffract or poorly diffract at about 1 Å to about 2 Å. With regard to the detecting methods described herein, the biomolecule can be any biomolecule described herein, including, e.g., a polypeptide, protein, polysaccharide, lipid (e.g., glycolipid, phospholipid, sterol), polynucleotide or nucleic acid (e.g., DNA or RNA). In exemplary embodiments, the biomolecule is a protein comprising one or more polypeptide chains. In exemplary instances, the biomolecule is an antibody or immunoglobulin, or an antigen-binding antibody fragment thereof, including any of those described herein under the section entitled "Biomolecules", In exemplary instances, the protein comprises one or more glycans, i.e., are glycanated biomolecules. In exemplary embodiments, the biomolecules are glycanated antibodies.

The following examples are given merely to illustrate the present invention and not in any way to limit its scope.

EXAMPLES

Example 1: Buffer Exchange of a Crystalline Monoclonal Antibody

The kSep® system (Sartorius Stedim North America, Inc., Bohemia, NY) is a counterflow gradient centrifugation system designed for biologics processing for harvesting cells as products or discarding cells and collecting the supernatant as product during manufacturing. This system is described in Kelly et al., Biotechnol. Prog. 32(6): 1520-1530 (2016) and U.S. Patent Publication No. 2011/0207222. The kSep® system differs from a traditional centrifugation system in that centrifugal forces are balanced by opposing forces of a continuous flow of fluids (e.g., media, buffer), creating a fluidized bed system of cells or particles within the apparatus. See, Dechsiri, C. (2004). Particle transport in fluidized beds: experiments and stochastic models Groningen: s.n. In a traditional centrifugation unit, a packed-bed system is achieved. The kSep® system also utilizes single-use components minimizing the need for cleaning and is conducive to aseptic processing through sterile welding connections. The kSep® system is available as a laboratory- or production-scale system. The kSep®400 system is a laboratory scale system that has the capacity to process 400 ml per cycle at a maximum flowrate of 114 L/hr. The kSep®400 system has four individual 100 ml chambers and each chamber can be run on its own or simultaneously with the others. The kSep®6000S system is a production scale system (see FIG. 1) that has the capacity to process 6000 ml per cycle at a maximum flowrate of 720 L/hr. The kSep®6000S system has six individual 1000 ml chambers and each chamber can be run on its own or simultaneously with the others.

While the kSep® system has been evaluated for its use in protein crystallization (McPherson, Methods 34(3): 254-265 (2004), it has not been used for further downstream processing. Here, the kSep® system is used to replace a hypertonic crystallization buffer with an isotonic formulation buffer suitable for patient administration, following a protein crystallization unit operation (see, e.g., FIG. 2). The kSep® system is also used in concentrating the protein crystallization suspension to a concentration amenable for patient dosing.

Using the kSep® system, a protein crystal suspension comprising a crystalline fully human monoclonal antibody was buffer exchanged with over 90% efficiency at one buffer exchange volumes and over 99% efficiency at two buffer exchange volumes. By altering the centrifugal force and fluid flow force balance within the kSep® system, the monoclonal antibody protein crystal suspension was concentrated prior to dispensing from the kSep® unit. Based on the amount of crystals loaded into the unit and the fluid flow force relative to the centrifugal force, the protein crystal suspension can be concentrated from 63 mg/ml to a range of 215 to 300 mg/ml. Counterflow gradient centrifugation via the kSep® system is therefore an effective means to buffer exchange crystallization buffer to formulation buffer and to concentrate protein crystals to concentrations that are amendable for patient administration.

Materials and Methods

Equipment: The kSep®400 unit was used for protein crystal suspension buffer exchange and concentration operations. The laboratory scale kSep® unit provided a platform to evaluate these operations without expending large amounts of material. In order to reduce the usage of material for the evaluation, the chamber usage was reduced from the standard four kSep® system chambers which would use at a minimum 400 ml to either two or one kSep® system chambers to reduce the volume usage to 100-300 ml. The concentrate-wash-harvest, CWH, disposable tubing set was used for this evaluation as its configuration provided a proper avenue to harvest the protein crystals after the buffer exchange and concentration unit operations.

Materials: A fully humanized monoclonal antibody was used for this evaluation. At the start of crystallization the antibody's formulation contained 20 mM sodium acetate, 220 mM Proline, and 0.01% polysorbate 80 at pH 5.0 with a concentration of 140 mg/ml. The crystallization buffer added to the system contained 16 mM sodium phosphate, 20% PEG 3350 at pH 8.4. The final protein crystal suspension at the conclusion of the crystallization unit operation consisted of approximately 9 mM sodium acetate, 98 mM Proline, 0.004% polysorbate 80, 7 mM sodium phosphate, 8.9% PEG 3350 at pH 6.2. The crystal concentration was 62.2 mg/ml.

Buffer Exchange buffer: The buffer used for buffer exchange and concentration was an isotonic buffer that consisted of the following components: 27 mM Succinic Acid, 15% PEG 3350, 0.1% PS80 at pH 5.2.

Results and Observations

Buffer Exchange

The buffer exchange operation was performed using the kSep® system's concentrate-wash-harvest pre-programmed application type (see, e.g., FIG. 3). The critical parameters that impacted the overall buffer exchange were the wash flowrate and the number of volumes per chamber (equivalent to diavolumes). The wash flowrate parameter impacted both processing time and buffer exchange efficiency. The higher the wash flowrate, the shorter the processing time, but the lower the buffer exchange efficiency. In converse, a lower wash flowrate increased the processing time, but improved the buffer exchange efficiency. For the number of volumes per chamber, volumes was defined by the bioreactor volume as specified in the kSep® system's recommended protocol. To quantify buffer exchange efficiency, the pH of the outlet stream was measured to observe the convergence of outlet pH with the buffer exchange buffer pH. The inlet feed material pH started at 6.2 and the buffer exchange buffer pH was 5.2, therefore the buffer exchange was considered complete once the outlet pH reached the pH of the buffer exchange buffer.

The results of the buffer exchange experiments are summarized in Table 1. Increasing the number of volumes per chambers improved the buffer exchange efficiency as the outlet pH from experiment 1 was 5.34 and the outlet pH from experiment 4 was 5.22. The other variables such as wash flowrate and feed volume also impacted the final outlet pH, but not to the same extent as the number of volumes per chamber.

TABLE 1

Buffer exchange experiments to evaluate key operating parameters

| Experiment | Feed Volume (ml) | Wash 1 Flowrate (ml/min) | Centrifugation Force (q) | # (volumes)/ chamber | Inlet Feed pH | Outlet pH | Buffer exchange buffer pH |
|---|---|---|---|---|---|---|---|
| 1 | 100 | 120 | 1000 | 1 | 6.2 | 5.34 | 5.2 |
| 2 | 100 | 70 | 1000 | 1 | 6.2 | 5.38 | 5.2 |
| 3 | 300 | 120 | 1000 | 1 | 6.2 | 5.38 | 5.2 |
| 4 | 100 | 120 | 1000 | 2 | 6.2 | 5.22 | 5.2 |
| 5 | 200 | 120 | 1000 | 2 | 6.2 | 5.27 | 5.2 |

Figure 2:
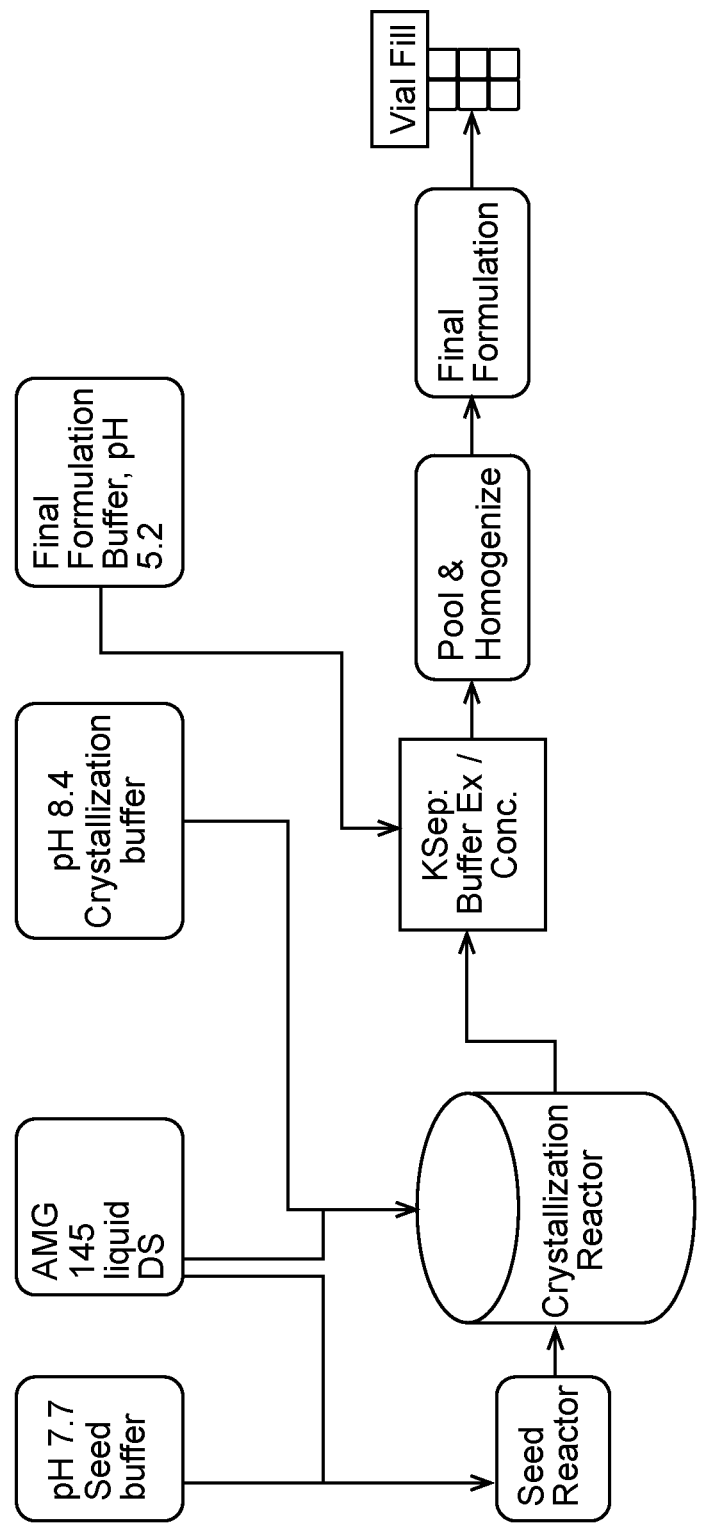
FIG. 2 is a Protein Crystallization Process Flow Diagram with the kSep® device.

The kSep® system performed better in terms of buffer exchange efficiency when compared to a traditional bench top centrifuge as shown in FIG. 2. After a single spin and decant operation for the bench top centrifuge (equivalent to one number of volumes per chamber in the kSep® system), the outlet pH was approximately 5.3 for the kSep® system. Feed volumes of 100 to 300 ml, wash 1 flowrates of 70 to 120 ml/min, and buffer exchange volumes of 1 to 2 were evaluated and determined the extent to which complete buffer exchanged occurred.

Concentrate

Following the buffer exchange operation, the protein crystal suspension was concentrated by altering the balance between the centrifugation force and the fluid flowrate. By having the centrifugation force greater than the fluid flowrate force, the protein crystals migrated towards one end of the kSep® system chamber and effectively concentrated within the chamber. Methods to achieve this outcome included: increasing the centrifugation force while keeping the fluid flowrate constant, decreasing the fluid flowrate while keeping the centrifugation force constant, or a combination of the previous two. There were two input variables that impacted the outlet concentration variable: wash flowrate/centrifugation force and feed volume. Using the wash 2 flowrate function with the kSep® system concentrate wash harvest program (see, e.g., FIG. 3), feed volumes from 150 to 300 ml and wash 2 flowrates of 20 to 35 ml/min were evaluated. Based on those input variables, concentrations ranging from 168 to 303 mg/ml were achieved using the kSep® as shown in Table 2.

TABLE 2

Concentration experiments to evaluate key operating parameters

| Experiment | Feed Volume (ml) | Wash 2 Flowrate (ml/min) | Centrifugation Force (g) | # (volumes)/chamber | Outlet Concentration (mg/ml) |
|---|---|---|---|---|---|
| 1 | 300 | 35 | 1000 | 1 | 303 |
| 2 | 200 | 35 | 1000 | 1 | 215 |
| 3 | 200 | 20 | 1000 | 1 | 235 |
| 4 | 200 | 35 | 1000 | 1 | 168 |
| 5 | 150 | 20 | 1000 | 1 | 201 |

Previous experiments concentrated the protein crystal suspension to outlet concentrations ranging from 122 to 229 mg/ml by altering the feed volume from 260 to 500 ml and maintaining the wash 2 flowrate at 30 ml/min. Even though outlet concentrations of greater than 200 mg/ml were observed, protein crystal agglomeration and crystallinity degradation were also observed via microscope with birefringence capability due to the use of a different Buffer Exchange buffer (10 mM NaPO4 pH6.2, 10% PEG3350, 120 mM Lysine, 0.1% Ps80 buffer (Lysine)). The results from the initial failed experiments are shown in Table 3.

TABLE 3

Results from Initial Experiments

| Experiment | Feed Volume (ml) | Wash 2 Flowrate (ml/min) | Centrifugation Force (g) | # (volumes)/chamber | Outlet Concentration (mg/ml) |
|---|---|---|---|---|---|
| 1 | 500 | 30 | 1000 | 0.6 | 215 |
| 2 | 400 | 30 | 1000 | 0.6 | 178 |
| 3 | 120 | 30 | 1000 | 1.5 | 129 |
| 4 | 270 | 30 | 1000 | 0.6 | 122 |
| 5 | 300 | N/A | 1000 | N/A | 229 |
| 6 | 300 | N/A | 1000 | N/A | 202 |

Harvest

After concentrating the protein crystal suspension to the desired concentration, the suspension must be dispensed (harvested) from the kSep® unit. Typically, in order to remove material from the kSep® system, the unit runs in reverse and pushes the material out through the kSep® chamber's inlet. The individual chamber peristaltic pumps pump in reverse to remove the material while the buffer pump pulses in buffer to prevent large pressure differentials from the inlet and outlet. The preprogrammed harvest operation in the kSep® concentrate-wash-harvest application is designed to harvest non-concentrated suspensions from the unit and as a result a number of initial experiments failed because either material clogged the disposable tubing in the unit or the packed crystal suspension was disrupted from the pulsing buffer pump or the individual chamber peristaltic pump.

The initial experiments used the pre-programmed harvest operation with a centrifugation speed at 60 g and a harvest (i.e. chamber peristaltic pump) flowrate at 50 ml/min. Using the pre-programmed operations resulted a number of failures in which material could not be harvested from the chamber. After a number of failed attempts at using the pre-programmed recipes, the harvesting operations was switched over to manual control in order to manipulate the flowrates and valve positioning on a real time basis. The centrifugation speed was decreased and kept at a constant value in order to reduce the number of conditions to evaluate and the buffer pump was kept on rather than pulsing buffer. The buffer pump was kept on so that there would be a constant increase in pressure from the flowrate of the buffer. The increase in pressure would gradually force the packed crystal suspension out of the chamber while the individual chamber peristaltic pumps would slowly pull material out of the crystal and prevent cavitation of the packed crystal suspension. Disrupting the packed crystal suspension would negatively impact the final crystal concentration. Table 4 summarizes experiments relating to harvesting packed (concentrated) crystal suspension from the kSep® system. Table 4 documents some of the harvest experiments and the observations noted during the experiment. The packed crystal suspension could not be harvested with the preprogrammed harvest automation as it was currently setup. The harvest operation needed to be switched into a manual operation in which the experimenter can adjust settings on a real time basis rather rely on automated controls. Experiments that are designated with an "a" and "b" are part of the same experiment where conditions were adjusted following a failed harvest attempt.

TABLE 4

| Expt | Program | Centrifugation Speed (g) | Chamber Pump Flowrate (ml/min) | Buffer Pump Flowrate (ml/min) | No. of Chambers in Use | Observation |
|---|---|---|---|---|---|---|
| 1 | Harvest Automation | 60 | 50 | N/A—controlled by automation | 1 | Material clogged in chamber |
| 2a | Harvest Automation | 80 | 50 | N/A—controlled by automation | 1 | Material clogged in chamber |
| 2b | Manual Intervention | 8 | 75 | 25 | 1 | Material removed from kSep chamber |
| 3a | Manual Intervention | 8 | 75 | 25 | 1 | Material clogged in chamber |
| 3b | Manual Intervention | 8 | 75 | 50 | 1 | Material removed from kSep chamber |
| 4 | Manual Intervention | 8 | 75 | 50 | 2 | Uneven harvest of chambers |
| 5 | Manual Intervention | 8 | 75 | 25 | 3 | Disruption of packed crystal suspension during harvest |
| 6 | Manual Intervention | 8 | 75 | 25 | 1 | Material removed from kSep chamber |
| 7 | Manual Intervention | 8 | 75 | 25 | 1 | Material removed from kSep chamber |
| 8 | Manual Intervention | 8 | 75 | 25 | 1 | Material removed from kSep chamber |

Figure 4:
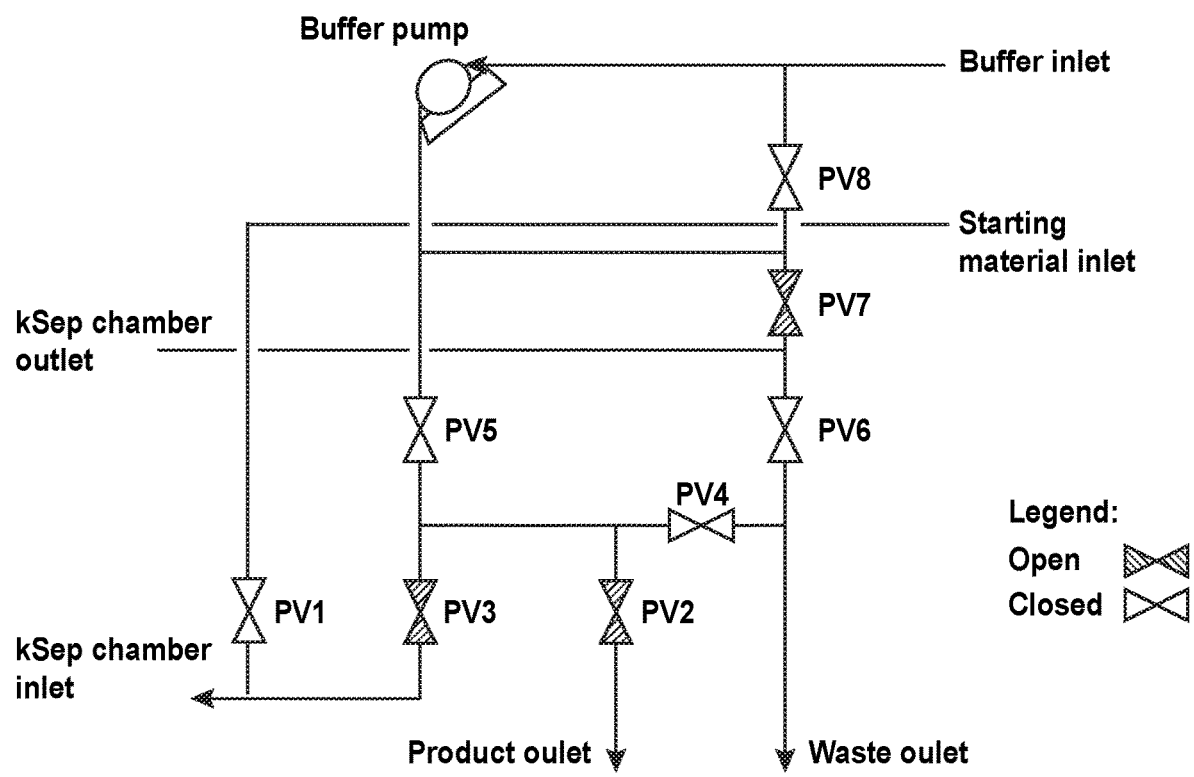
FIG. 4 is a kSep® system piping and instrumentation diagram/drawing for harvest evaluation.

Another factor to consider is the individual chamber pumps; the individual chamber pumps need to pull the material out of the chamber without causing any cavitation within the packed crystal suspension. Cavitation disrupts the concentration profile and creates a non-uniform concentration gradient across the concentrated crystal suspension as documented in Table 4 experiments 4 and 5. To harvest the concentrated crystal suspension, one chamber was harvested at a time. Harvesting multiple chambers at once increased the likelihood of cavitation. The centrifugation force was kept at 8 g, the buffer pump was set from 25-50 ml/min and the individual chamber pump was set to 75 ml/min (FIG. 4). The centrifugation force and buffer pump create the driving force to push the material out of the chamber while the individual chamber pump acts as a pulling mechanism to ensure cavitation is limited.

Example 2: Distinguishing

Washing of samples in Formulation Buffer: Samples of crystalline material were prepared in a batch method as essentially described in International Patent Application Publication No. WO2016010927, entitled "CRYSTALLINE ANTIBODY FORMULATIONS" which is incorporated by reference in its entirety.

All samples were washed in a formulation buffer of 27 mM succinic acid and 15% PEG 3350 and 0.1% Tw-80, pH=5.5. One mL of the crystals or amorphous material was combined with 1 mL of formulation buffer in an Eppendorf tube and mixed by gentle inversion. The mixture was then centrifuged for 5 mins at 2000 RPM=376 rcf and the supernatant removed. Another 1 mL of formulation buffer was added and the pellet resuspended and mixed gently followed by centrifugation. This was repeated once.

Sample Packing: All samples were packed in 4.0 mm Bruker rotors. A 1 mL pipet tip was cut to act as a funnel into the rotor and sized so that the rotor and funnel fit inside a 2.0 mL Eppendorf tube. Samples were packed by adding 100 µL of the suspension to the funnel and then centrifuged at 10 k rcf for 2 mins. This was repeated 4-8 times until the rotor was well-packed with solid sample.

SSNMR: A Bruker Ascend Avance III widebore spectrometer operating at $^1$H resonance frequency of 500 MHz was used for analysis. A 4 mm H/F/X MAS probe operating at a spinning frequency of 4 kHz was used for all experiments, except when noted otherwise. A BCU II −80/60 temperature unit was used to control temperature to 300 K, except when doing temperature studies. $^1$H 2.5 us pi/2=160 W were used for 90 degree pulses. $^1$H CPMG spectra were collected with 20 pi pulses of 5 µs separated by 500 µs for a total 10 ms of CPMG pulses suppressing signals from solid material. After measuring the CPMG spectra the samples were spun up to 14 kHz and a 13C cross polarization (CP) was measured as a way to calibrate the total solid material in the rotor and account for differences in packing between samples and rotors. The CP spectra used a 2 ms contact time and 50 kHz RF spin lock pulse on 13C and appropriately matched ramp pulse on $^1$H.

Observations

Figure 5:
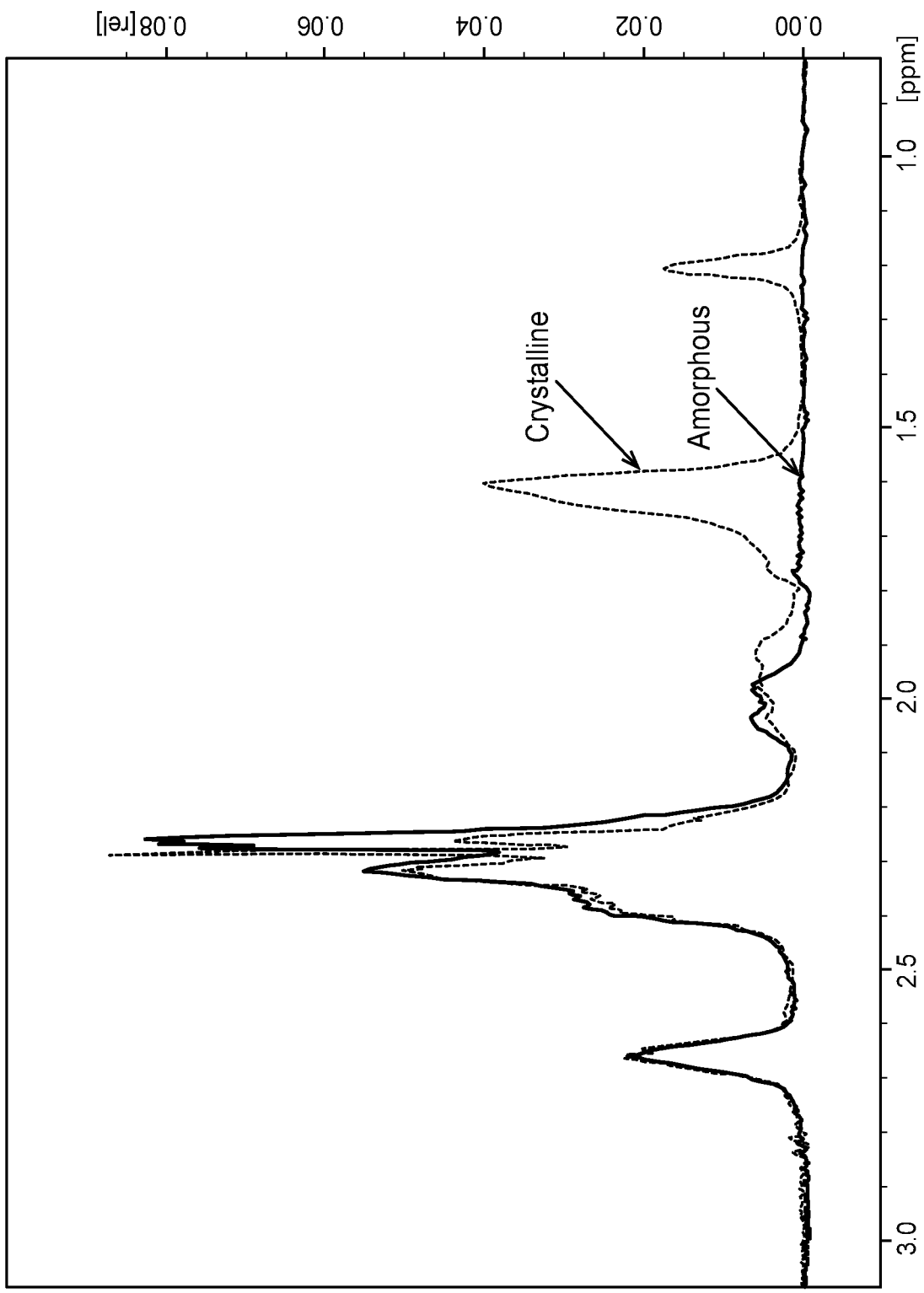
FIG. 5 is a $^1$H NMR CPMG spectra of crystalline (red) vs. amorphous (blue) material.
Figure 6:
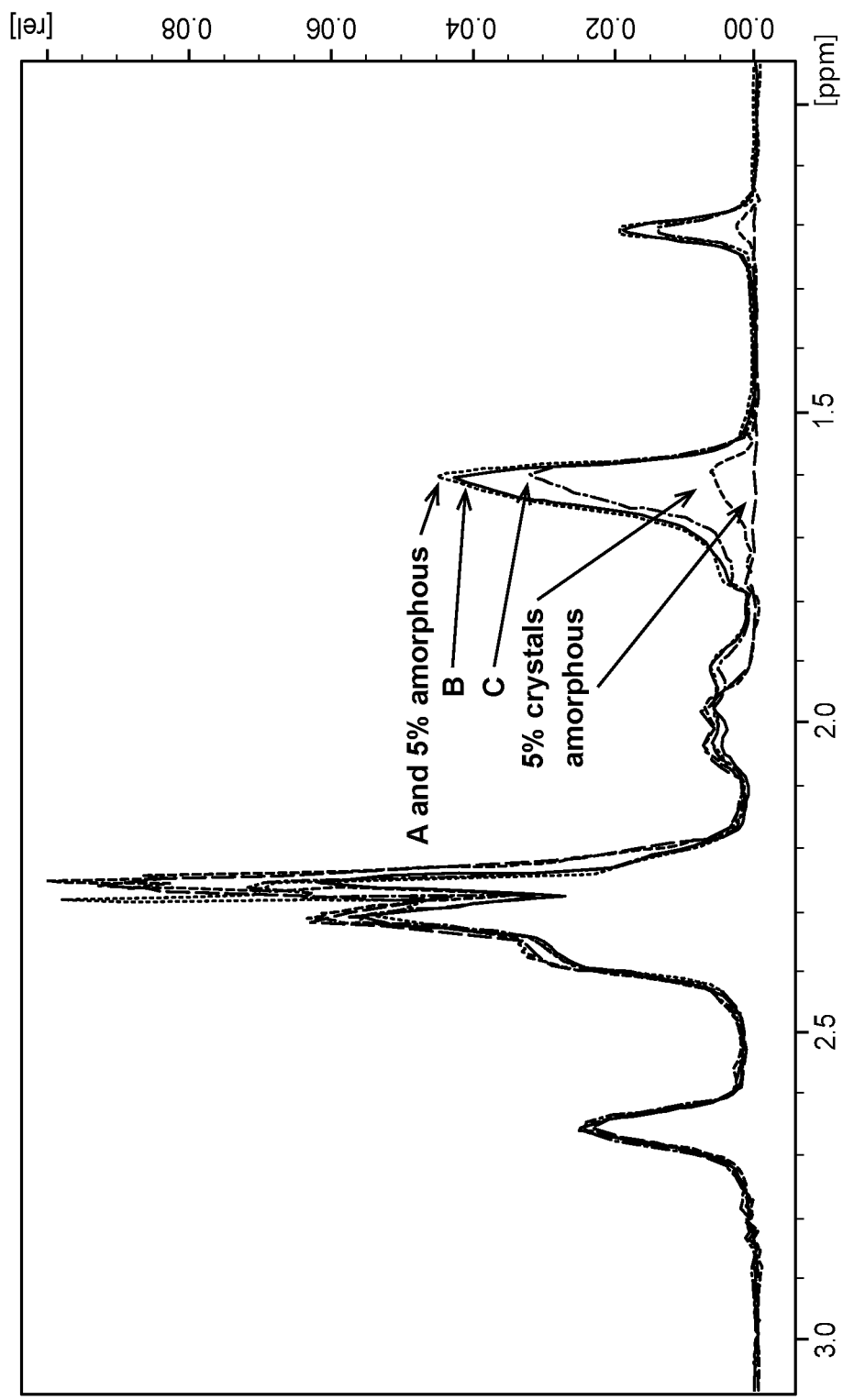
FIG. 6 is a $^1$H NMR CPMG spectra of various preparations of crystalline material between 100% and 0% showing the possibility of quantitation. Preparations A, B, and C contain decreasing amounts of crystals. "5% amorphous" is a preparation containing crystals with 5% amorphous material and "5% crystals" is a preparation containing amorphous material with 5% crystals.
Figure 7:
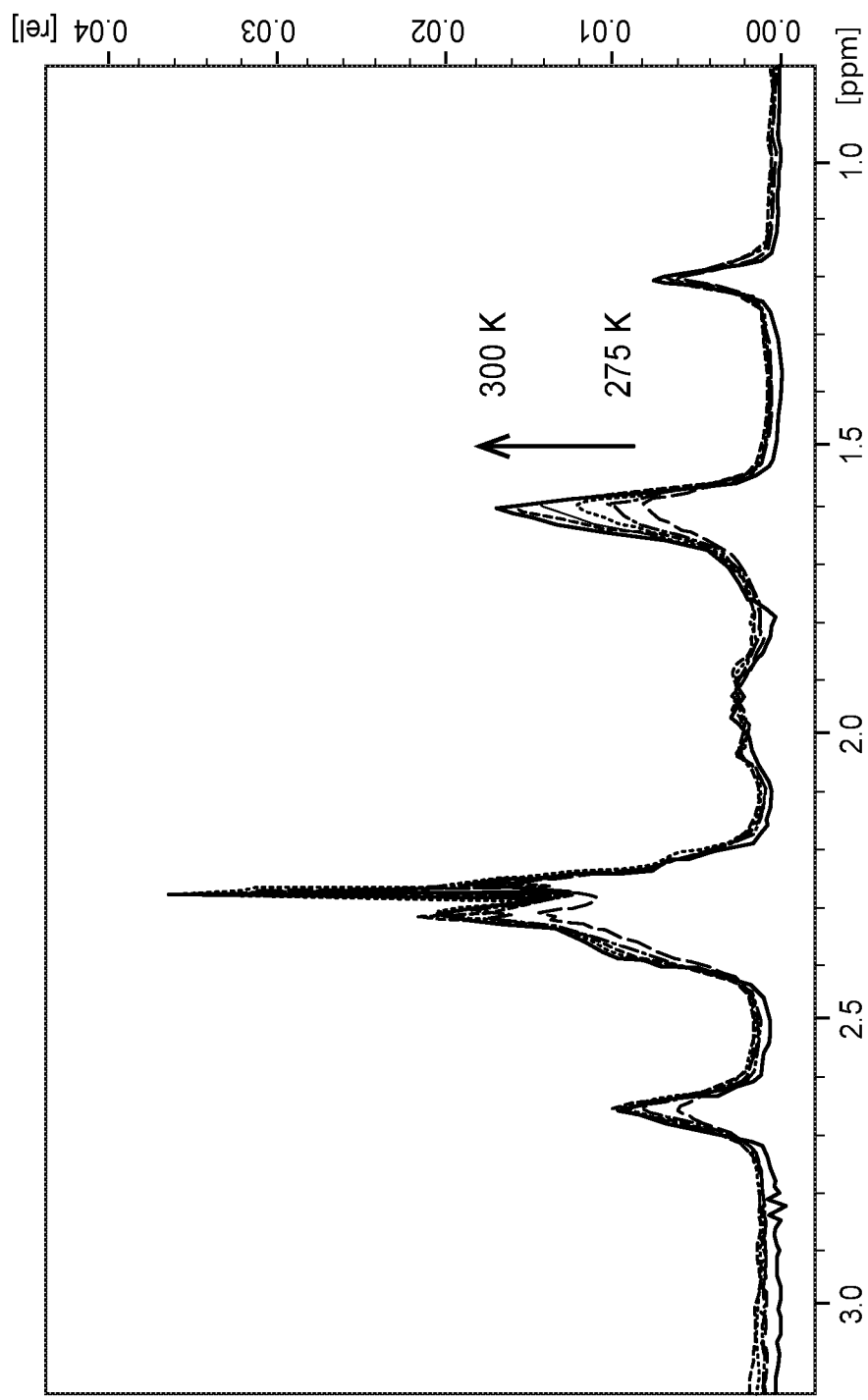
FIG. 7 is a $^1$H NMR CPMG spectra vs. temperature showing that the intensity of the peaks increases with temperature indicating that mobility is increasing.

The CPMG spectra were used to suppress proton signals arising from parts of the sample that are in the solid state and not mobile. In the CPMG spectra of the mAb crystals and amorphous product, there were some signals that appeared in the crystalline material that did not appear in the amorphous material (see FIG. 5). These signals could be used to quantify the amount of crystalline content as shown with the spectra from samples spiked with either 5% crystalline or 5% amorphous mAbs (FIG. 6). The signals in the crystalline spectra also increased with increasing temperature, indicating that those parts of the molecule were becoming more mobile (FIG. 7).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments can become apparent to those of ordinary skill in the art upon reading the foregoing description. The inventors expect skilled artisans to use such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of preparing a composition comprising crystalline biomolecules, comprising:

a) forming a fluidized bed of crystalline biomolecules in a rotating chamber comprising an inlet and an outlet, wherein the fluidized bed is created by rotating the chamber about a substantially horizontal axis to create a centrifugal force ($F_{centrifugal}$) in said chamber, flowing a first stream of a first solution through the inlet in a direction opposite to the direction of the $F_{centrifugal}$ and at a first flow rate (FR1) having a force ($F_{FR1}$) which counter balances $F_{centrifugal}$, and collecting the first solution from the chamber while substantially maintaining the formation of the fluidized bed of crystallized biomolecules;

b) performing step (i), (ii), or (iii):

i. flowing a second stream of a second solution to replace the first stream of the first solution while substantially maintaining the formation of the fluidized bed of crystallized biomolecules;

ii. concentrating the crystallized biomolecules within a region of the chamber by changing FR1 to a second flow rate (FR2) having a force ($F_{FR2}$) which is less than $F_{centrifugal}$ or by increasing the speed of rotation of the chamber to increase $F_{centrifugal}$ to a level which is greater than $F_{FR1}$;

iii. a combination of step (i) and step (ii); and c) flowing a second stream into the chamber through the outlet in a direction which is parallel to the direction of the $F_{centrifugal}$ to crystalline remove the crystalline biomolecules from the chamber.

2. The method of claim 1, wherein $F_{centrifugal}$ is 1000 g during at least step (i).

3. The method of claim 1, wherein the feed volume of the second stream of the second solution is about 50 to about 500 ml during step (i).

4. The method of claim 1, wherein (A) the number of volumes of the first solution per chamber is 2 or more during step (i), (B) FR1 is about 50 ml/min to about 150 ml/min during step (i), (C) the first solution is a hypertonic crystallization buffer, (D) the second solution is an isotonic formulation buffer, (E) the second solution is an isotonic formulation buffer, (F) the $F_{centrifugal}$ is 1000 g during step (ii), (F) the feed volume of the second stream of the second solution is about 100 to about 500 ml during step (ii), (G) the number of volumes of the first solution per chamber is 1 or 2 during step (ii), (H) FR2 is about 10 ml/min to about 50 ml/min during step (ii), (I) the concentration of the crystalline biomolecules is increased at least 2-fold, (J) the method comprises decreasing $F_{centrifugal}$ to a level of about 5 g and about 20 g, (K) FR1 is controlled by a first pump and the first pump is set to about 10 ml/min to about 100 ml/min after step (b), (L) the rotating chamber is connected to a chamber peristaltic pump, (M) the method is carried out in an apparatus comprising more than one rotating chamber, (N) the crystalline biomolecule is a protein or comprises one or more polypeptide chains, or (O) any combination thereof.

5. The method of claim 4, wherein the concentration of the crystalline biomolecules is increased at least 3-fold or at least 4-fold.

6. The method of claim 4, wherein the chamber peristaltic pump is set to pump in the same direction of the first pump and $F_{centrifugal}$.

7. The method of claim 4, wherein the chamber peristaltic pump is set to about 75 ml/min, the first pump is set to about 50 ml/min, and $F_{centrifugal}$ is decreased to below 10 g.

8. The method of claim 4, wherein the apparatus comprises at least 2, at least 4 or at least 6 rotating chambers.

9. The method of claim 8, wherein steps (a) to (c) are carried out in more than one chamber.

10. The method of claim 9, wherein crystalline biomolecules are removed from a chamber of the apparatus at a time distinct from when crystalline biomolecules are removed from another chamber of the apparatus.

* * * * *